United States Patent
Mizutani et al.

(10) Patent No.: US 7,445,615 B2
(45) Date of Patent: Nov. 4, 2008

(54) INTERLABIAL PAD

(75) Inventors: Satoshi Mizutani, Kanonji (JP); Wataru Yoshimasa, Kanonji (JP); Megumi Tokumoto, Kanonji (JP)

(73) Assignee: Uni-Charm Corporation, Ehime-Ken (JP)

( * ) Notice: Subject to any disclaimer, the term of this patent is extended or adjusted under 35 U.S.C. 154(b) by 0 days.

(21) Appl. No.: 11/349,493

(22) Filed: Feb. 6, 2006

(65) Prior Publication Data

US 2006/0200108 A1 Sep. 7, 2006

(30) Foreign Application Priority Data

Mar. 4, 2005 (JP) .............................. 2005-061645

(51) Int. Cl.
*A61F 13/15* (2006.01)
(52) U.S. Cl. .............................. 604/385.17; 604/385.18; 604/385.01; 604/385.02; 604/386; 604/384; 604/904
(58) Field of Classification Search ............ 604/385.02, 604/385.17, 385.18, 385.01, 385.04, 904, 604/11–18; D24/141
See application file for complete search history.

(56) References Cited

FOREIGN PATENT DOCUMENTS

| | | |
|---|---|---|
| JP | 2001-506168 A | 5/2001 |
| JP | 2004-097693 A | 4/2004 |
| JP | 2004-121611 A | 4/2004 |
| JP | 2004-261230 A | 9/2004 |
| JP | 2004-261231 A | 9/2004 |
| WO | WO-98/57608 A1 | 12/1998 |
| WO | WO 9901093 | 1/1999 |
| WO | WO-02/094147 A1 | 11/2002 |
| WO | WO-02/094152 A1 | 11/2002 |
| WO | WO-02/094153 A1 | 11/2002 |
| WO | WO-02/094156 A1 | 11/2002 |
| WO | WO-02/094161 A1 | 11/2002 |
| WO | WO-02/094163 A1 | 11/2002 |

*Primary Examiner*—Jacqueline F. Stephens
(74) *Attorney, Agent, or Firm*—Darby & Darby P.C.

(57) ABSTRACT

An interlabial pad fits a vaginal opening and a vestibule floor without a gap with the vaginal opening or the vestibule floor. The pad prevents leakage of menstrual blood from a gap and prevents dropping out of the pad when the pad is worn between labia. The interlabial pad is provided with an absorbent body for absorbing and holding body fluid, has a central axis, and is worn with at least one portion held by labia minora, between the labia, so that at least one portion close to the central axis when worn touches the vestibule floor inside the labia of the wearer, and is also provided with a rear portion low compression rigidity structure, so that a rear portion that is positioned to the rear of the wearer and, when worn, touches the body of the wearer first, has low compression rigidity in comparison to a front portion positioned to the front.

8 Claims, 8 Drawing Sheets

INTERLABIAL PAD

This application is based on and claims the benefit of priority from Japanese Patent Application No. 2005-061645, filed on 4 Mar. 2005, the content of which is incorporated herein by reference.

BACKGROUND OF THE INVENTION

1. Field of the Invention

The present invention relates to an interlabial pad that can be made to fit a vaginal opening and a vestibule floor without a gap with the vaginal opening or the vestibule floor occurring, the pad enabling leakage of menstrual blood from a gap to be prevented, and dropping out of the pad to be avoided, when a wearer wears the pad between labia.

2. Related Art

Conventionally, sanitary napkins or tampons are generally used as sanitary products for women. With regard to the sanitary napkins, considerable efforts have been made to prevent leakage of menstrual blood from a gap that occurs due to poor contact with the vicinity of the vaginal opening. Moreover, in the case of tampons, due to product attributes thereof, a foreign object sensation or a feeling of discomfort when worn, or difficulty in fitting inside the vagina occurs, and considerable efforts have been made to eliminate these.

Under these circumstances, as a sanitary product in between a sanitary napkin and a tampon, in recent years, an interlabial pad (referred to below as a pad) is receiving attention as a sanitary product. This interlabial pad is worn with a portion thereof inserted between the labia, and is made to contact the inner surface of the labia; since contact with the body is good compared to that of sanitary napkins, leakage of menstrual blood is inhibited; and since the menstrual blood is prevented from spreading and coming into wider contact with the body, it is hygienic and clean. Moreover, since it is smaller than a sanitary napkin, it is comfortable and has excellent wearability, and compared to a tampon that is inserted into the vagina, it is distinguished in that little psychological resistance is caused when worn.

However, since the interlabial pad adheres to the body due to interlabial sandwiching force, it has to flexibly follow movements of the labia to the left and right caused by the wearer's movements. In cases in which it is difficult for the interlabial pad to follow the body movements, there is a danger that it may drop out of the wearer's labia. As a result, various types of interlabial pads, with which better adherence to the body is possible, have been considered.

The interlabial pad described in Japanese Patent Application, Laid Open No. 2001-506168 (referred to below as Patent Document 1) is formed of a fluid permeable top sheet, a back sheet that is difficult for fluids to permeate, and an absorbing body disposed therebetween, with a "bending axis" preferably provided along a center line in a longitudinal direction of the interlabial pad. By bending the pad along this "bending axis" and inserting between the labia of the wearer, since the top sheet of the pad maintains contact with an inner wall of the labia of the wearer and has a uniform covering area, it can be prevented from dropping out.

A "bending axis" of an interlabial pad as described in Patent Document 1 is a line or axis about which the pad has a tendency to be bended or folded when a compressing force towards an inner is received from a side of the pad in a lateral direction. In the Patent Document 1, outside of the center line in the longitudinal direction that is the "bending axis", the interlabial pad has a uniform thickness, and the "bending axis" is formed by making its rigidity lower than that of other portions, with respect to any or all of a top sheet, an absorbing body, and a back sheet. That is, since rigidities differ between the "bending axis" and "other portions", a crest of the fold at the "bending axis" has a uniform rigidity in the longitudinal direction.

Figure 16:
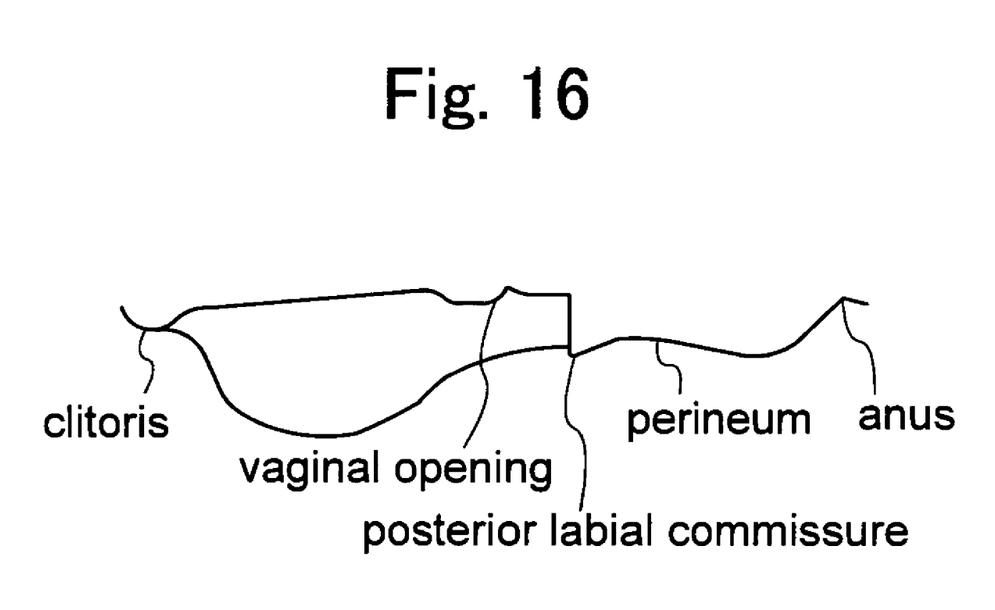
FIG. 16 is an explanatory view of an interlabial pad.

Here, the interlabial pad is worn so as to be held between left and right labia minora linking clitoris and posterior labial commissure, as shown in FIG. 16. The vestibule floor within the labia minor is located more within the body than the clitoris and the posterior labial commissure, and a central axis in the body connecting the clitoris to the perineum has an uneven rather than a straight line contour. In order to prevent leakage of menstrual blood when wearing the interlabial pad, the interlabial pad has to be of a size that covers more towards the front than the clitoris, and more towards the rear than the posterior labial commissure.

As a result, when a wearer wears the interlabial pad between the labia minora, even when the central axis extending in the longitudinal direction of the pad is made to fit the vaginal opening and the vestibule floor, a rear portion of the pad touches the posterior labial commissure that protrudes out from the body more than the vaginal opening and the vestibule floor. When the rear portion of the pad touches the body, the central axis in the longitudinal direction of the pad does not reach as far as the vaginal opening and the vestibule floor, so that a gap occurs between the pad, and the vaginal opening and the vestibule floor. Furthermore, if the pad is forcibly inserted so as to fit the central axis in the longitudinal direction of the pad, with the vaginal opening and the vestibule floor, there has been a risk that the pad, having uniform rigidity in its longitudinal direction, may buckle irregularly and contact with the labia inner wall may deteriorate, so that the pad may drop down from the labia, and also there has been a risk that excessive irritation may be given to the labia.

SUMMARY OF THE INVENTION

The present invention has been made in consideration of the above problems, and an object thereof is the provision of an interlabial pad that can be made to fit a vaginal opening and a vestibule floor without a gap with the vaginal opening or the vestibule floor occurring, the pad enabling leakage of menstrual blood from a gap to be prevented, and dropping out of the pad to be avoided, when a wearer wears the pad between labia.

The inventors of the present invention put considerable research effort into fitting a central axis in a longitudinal direction of the pad, to the vaginal opening and the vestibule floor, and improving contact with labia inner wall, when the pad is worn between the labia minora. As a result, it was found that by making a rear portion of the pad, located towards the rear of the wearer, easily indent first, compared to a front portion, when the pad is worn between the labia, even if the rear portion of the pad comes in contact with the posterior labial commissure, the contact portion indents first, and a state can be ensured in which there is contact between the central axis of the pad and the vaginal opening and the vestibule floor, leading to the realization of the present invention. More specifically, the present invention is as follows.

In a first aspect of the present invention, an interlabial pad having a central axis and provided with an absorbent body for absorbing and holding body fluid, is worn with at least one portion held between the labia minora of the labia, so that at least one portion close to the central axis, when worn, touches the vestibule floor inside the labia of a wearer, and the interlabial pad includes a rear portion low compression rigidity structure to provide low compression rigidity at a rear portion, so that the rear portion that is positioned to the rear of the wearer and, when worn, touches the body of the wearer first, has low compression rigidity in comparison to a front portion positioned to the front.

According to the first aspect of the present invention, the interlabial pad has the rear portion low compression rigidity structure, by which the rear portion that is positioned to the rear of the wearer and, when worn, touches the body of the wearer first, has low compression rigidity in comparison to the front portion positioned to the front. Here, the "front portion" and the "rear portion" do not necessarily imply that the pad is in two equal portions, and the boundary between the "front portion" and the "rear portion" may be positioned more to the rear than a position at which the central axis of the pad when worn touches the vaginal opening. Moreover, in cases in which areas with different compression rigidities are arranged in multiple places in the front portion, the compression rigidity of the rear portion is set lower than at least the compression rigidity of the boundary area of the rear portion with the front portion.

The interlabial pad according to the first aspect of the present invention is provided with the rear portion low compression rigidity structure, and the rear portion of the pad that, when worn, touches the body of the wearer first, indents first. As a result, when the pad is worn interlabially, even if the rear portion of the pad is in contact with the posterior labial commissure that protrudes outwards from the body more than the vaginal opening or the vestibule floor, the rear portion of the pad indents first, and it is possible to maintain a state in which the vaginal opening and the vestibule floor are in close contact with the central axis of the pad. Therefore, according to the interlabial pad related to the first aspect of the present invention, it is possible to avoid leakage of menstrual blood from a gap and the pad dropping out.

According to a second aspect of the interlabial pad as described in the first aspect of the present invention, a compression rigidity value of the rear portion is smaller than a compression rigidity value of the front portion, the difference being greater than or equal to $0.1$ $N/cm^2$, and less than or equal to $0.9$ $N/cm^2$.

Figure 1:
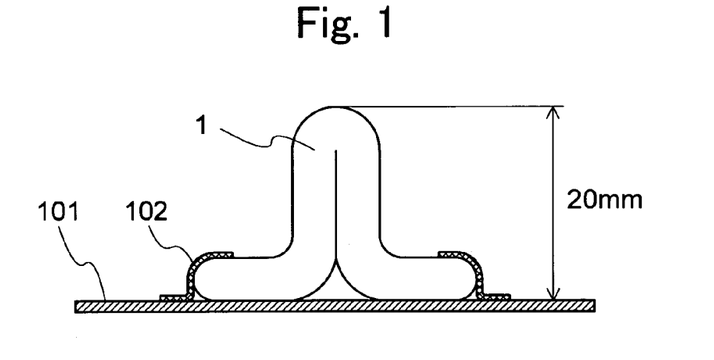
FIG. 1 is a view that explains a method for measuring a compression rigidity value.

In the interlabial pad according to the second aspect of the present invention, the compression rigidity value of the rear portion of the pad is designed to be smaller than the compression rigidity value of the front portion by a value greater than or equal to $0.1$ $N/cm^2$ and less than or equal to $0.9$ $N/cm^2$. The difference between the compression rigidity values is more preferably greater than or equal to $0.1$ $N/cm^2$ and less than or equal to $0.5$ $N/cm^2$. Here, the "compression rigidity value" is measured based on a measuring method by a KES system, and using a measuring instrument manufactured by Kato Tech, Co., Ltd., (KES-5 Handy-Type Compression Tester), it is measured under conditions of a loading of $100$ $g/cm^2$, a compression terminal area of $1$ $cm^2$, a terminal speed of $0.1$ cm/sec, and a gap of $20$ mm. More specifically, under these conditions, as shown in FIG. 1, with the pad 1 fixed to a measuring table 101 using tape 102 so that measuring range height from the central axis of the pad 1 is $20$ mm, a force required to compress the central axis of the pad 1 by $3$ mm in a vertical direction when worn, is used. With this type of interlabial pad, even if the rear portion of the pad when worn is in contact with the posterior labial commissure, since the rear portion of the pad can indent first, the pad can be made to fit the vaginal opening and the vestibule floor without a gap occurring with the vaginal opening or the vestibule floor, and it is possible to effectively avoid leakage of menstrual blood from a gap and the pad dropping out.

In a third aspect of the interlabial pad as described in the first or the second aspect of the present invention, the device to realize rear portion low compression rigidity is a slit implemented in a region straddling the central axis of the rear portion.

In the interlabial pad according to the third aspect of the present invention, as the rear portion low compression rigidity structure, a slit is provided in a region straddling the central axis of the rear portion. The slit provided in the "region straddling the central axis", is, for example, arranged symmetrically about the central axis, in a direction approximately perpendicular to the central axis. Alternatively, a slit arranged in a direction approximately perpendicular to the central axis and a slit arranged approximately parallel to the central axis may be combined. Furthermore, a slit in an oblique direction to the central axis may be provided. Moreover, the number of slits is not particularly limited, and multiple slits may be arranged.

According to the interlabial pad related to the third aspect of the present invention, since the central axis is divided by the slit, even if the rear portion of the pad when worn is in contact with the posterior labial commissure, only the rear portion of the pad indents first and is in a compressed state. At this time, the compression force that the rear portion of the pad, in contact with the posterior labial commissure, receives, is not transmitted to the front portion of the pad that is divided by the slit. Accordingly, the portion that is to the front of the slit, that is the rear portion low compression rigidity structure, hardly receives any compression force when worn, and the pad can be made to fit the vaginal opening and the vestibule floor, so that the leakage of menstrual blood from a gap and dropping out of the pad can be avoided.

In a fourth aspect of the interlabial pad as described in any of the first, second, or third aspects of the present invention, the rear portion low compression rigidity structure is an embossment implemented in a region straddling the central axis of the front portion.

In the interlabial pad according to the fourth aspect of the present invention, as the rear portion low compression rigidity structure, the embossment is implemented in a region straddling the central axis of the front portion. The embossment implemented in the "area straddling the central axis", is, for example, arranged symmetrically about the central axis, at equal intervals, in a row in a direction approximately perpendicular to the central axis. Alternatively, the arrangement may include multiple rows, or may be a continuous embossment pattern. There is no particular limitation to the embossment pattern, and a dot pattern, a grid pattern, a wave pattern, or the like may be cited.

According to the interlabial pad of the fourth aspect of the present invention, since the region on which the embossment is provided has high density in parts, as a result, a difference in rigidity is arranged in the central axis direction. That is, the region in which the embossment is arranged is a high rigidity area that divides the front portion and the rear portion of the pad, and when the interlabial pad is worn, in cases in which the rear portion of the pad is in contact with the posterior labial commissure, the embossed region serves as a trigger for bending, and the rear portion of the pad only indents first, and is compressed. At this time, since the rigidity of the embossed region is high, the compression force that the pad receives on coming in contact with the posterior labial commissure is not easily transmitted to the portion of the pad that is to the front of the embossed region. Accordingly, the portion that is to the front of the embossment, that is the rear portion low compression rigidity structure, hardly receives any compression force when worn, and the pad can be made to fit the vaginal opening and the vestibule floor, so that the leakage of menstrual blood from a gap and dropping out of the pad can be avoided.

In a fifth aspect of the interlabial pad as described in any of the first to the fourth aspects of the present invention, the rear portion low compression rigidity structure is a part of the absorbent body which has a lower basis weight per unit area in a rear portion relative to that of a front portion.

In the interlabial pad according to the fifth aspect of the present invention, as the rear portion low compression rigidity structure, a part of the absorbent body positioned in the rear portion has a lower basis weight per unit are than a basis weight per unit area of a part thereof positioned in a front portion. The region with the lower basis weight per unit area forms at least a border region of the rear portion with the front portion, and if a region with areas straddling the central axis is included, may form the whole of the rear portion of the pad.

According to the interlabial pad related to the fifth aspect of the present invention, since the region in which the part with lower basis weight per unit area has a density lower than that of surrounding regions, in cases in which force from the wearer in the vertical direction is applied to the pad, the compression rigidity of that area is low. As a result, when the interlabial pad is worn, in cases in which the rear portion of the pad is in contact with the posterior labial commissure, the region with lower basis weight per unit area serves as a trigger for bending, and the rear portion of the pad only indents first, and is compressed. At this time, the compression force the pad receives on coming in contact with the posterior labial commissure is not easily transmitted to the portion of the pad more towards the front than the region with the light coating. Accordingly, the portion that is to the front of the region with lower basis weight per unit area, that is the rear portion low compression rigidity structure, hardly receives any compression force when worn, and the pad can be made to fit the vaginal opening and the vestibule floor, so that the leakage of menstrual blood from a gap and dropping out of the pad can be avoided.

In a sixth aspect of the interlabial pad as described in any of the first to the fifth aspects of the present invention, the rear portion low compression rigidity structure is a part of the absorbent body which is formed of materials of different compression rigidities, and a material forming a front portion of the absorbent body has a high compression rigidity relative to a material forming a rear portion.

In the interlabial pad according to the sixth aspect of the present invention, as the rear portion low compression rigidity structure, a compression rigidity of a material forming a part of the absorbent body in the front portion is higher than the compression rigidity of a material forming another part of the absorbent body in the rear portion. In the front portion, the region with the high compression rigidity forms at least a border region with the rear portion, and if the region with the area straddling the central axis is included, may form the whole of the front portion of the pad.

In the interlabial pad according to the sixth aspect of the present invention, since the compression rigidity of the rear portion of the pad is lower than the compression rigidity of the front portion, when the interlabial pad is worn, in cases in which the rear portion of the pad is in contact with the posterior labial commissure, the part formed of the material with the high compression rigidity serves as a trigger for bending, and the rear portion of the pad only indents first, and is compressed. At this time, because the material with the high compression rigidity exists in the front portion of the pad, the compression force that the pad receives on coming in contact with the posterior labial commissure is not easily transmitted to the front portion of the pad. Accordingly, the front portion in which the material with the high compression rigidity exists, being the rear portion low compression rigidity structure, hardly receives any compression force when worn, so that the pad can be made to fit the vaginal opening and the vestibule floor, and the leakage of menstrual blood from a gap and the pad dropping out can be effectively avoided.

In a seventh aspect of the interlabial pad as described in any of the first to the sixth aspects of the present invention, the interlabial pad is folded in two with the central axis as a folding axis, the rear portion low compression rigidity structure is a cutting that extends from a border of the rear portion, in the direction of the central axis, and the cutting has a prescribed width and does not reach as far as the central axis.

In the interlabial pad according to the seventh aspect of the present invention, as the rear portion low compression rigidity structure, the cutting is made extending from the border of the rear portion, in the direction of the central axis. This cutting has a prescribed width, does not reach as far as the central axis, and outside of the vicinity of the central axis, divides the pad in two.

In the interlabial pad according to the seventh aspect of the present invention, by the existence of the cutting, outside of the vicinity of the central axis, the pad is divided into the front portion and the rear portion. As a result, when the interlabial pad is worn, in cases in which the rear portion of the pad is in contact with the posterior labial commissure, the rear portion of the pad in which the cutting is made, opens from a folded state, indents first, and is compressed. At this time, since the front portion of the pad is divided by the cutting, the compression force the pad receives on coming in contact with the posterior labial commissure is not easily transmitted. Accordingly, the portion to the front of the area in which the cutting exists, being the rear portion low compression rigidity structure, hardly receives any compression force when worn, so that the pad can be made to fit the vaginal opening and the vestibule floor, and the leakage of menstrual blood from a gap and the pad dropping out can be effectively avoided.

In an eighth aspect of the interlabial pad as described in any of the first to the seventh aspects of the present invention, the interlabial pad is folded in two with the central axis as a folding axis, having two folded parts facing each other, and rear portion low compression rigidity structure is a joining structure for joining parts of the two folded parts in the front portion.

In the interlabial pad according to the eighth aspect of the present invention, although the folded parts in the front portion of the pad are joined, the folded parts in the rear portion are not joined. That is, folding of the parts joined in the front portion of the pad is controlled, but the folding in the rear portion is not controlled.

Therefore, according to the interlabial pad related to the eighth aspect of the present invention, in the front portion of the pad, in which the folding is controlled by the joining, the pad cannot open, but in the rear portion of the pad that is not joined, the folded pad can open easily. As a result, when the interlabial pad is worn, in cases in which the rear portion of the pad is in contact with the posterior labial commissure, the rear portion of the pad only, that is not joined, indents first, by the folded parts opening, and is compressed. At this time, since the front portion of the pad is not joined, it is not easily deformed by the compression force the pad receives on coming in contact with the posterior labial commissure. Accordingly, the front portion in which the joining structure is implemented, being the rear portion low compression rigidity structure, hardly receives any compression force when worn, so that the pad can be made to fit the vaginal opening and the vestibule floor, and the leakage of menstrual blood from a gap and the pad dropping out can be effectively avoided.

In a ninth aspect of the interlabial pad as described in any of the first to the eighth aspects of the present invention, a part of the front portion additionally has a front portion low compression rigidity structure, having low compression rigidity in comparison to other locations in the front portion.

The interlabial pad according to the ninth aspect of the present invention, besides the rear portion low compression rigidity structure, at the same time has the front portion low compression rigidity structure. In this way, when the pad is worn, not only in cases in which the rear portion of the pad is in contact with the posterior labial commissure, but also in cases in which the front portion of the pad is in contact with the clitoris at the same time, both the front portion and the rear portion can indent. As a result, the pad does not deform irregularly when worn, so that the central axis of the pad can be made to fit the vaginal opening and the vestibule floor, and the leakage of menstrual blood from a gap and the pad dropping out can be effectively avoided.

According to the present invention, an interlabial pad is provided that can be made to fit a vaginal opening and a vestibule floor without a gap with the vaginal opening or the vestibule floor occurring, that can prevent leakage of menstrual blood from a gap, and with which dropping out of the pad can be avoided, when a wearer wears the pad between labia. Furthermore, the interlabial pad that is provided does not deform irregularly when worn, and excessive irritation to the labia can be prevented.

DETAILED DESCRIPTION OF THE INVENTION

Below, embodiments of the present invention are explained, referring to the figures. Furthermore, in explanations of each embodiment outside of Embodiment 1, items that are the same or similar to those in Embodiment 1 are given the same reference symbols, and explanations thereof are omitted or abbreviated.

EMBODIMENT 1

Slit

Overall Configuration of Interlabial Pad

Figure 2:
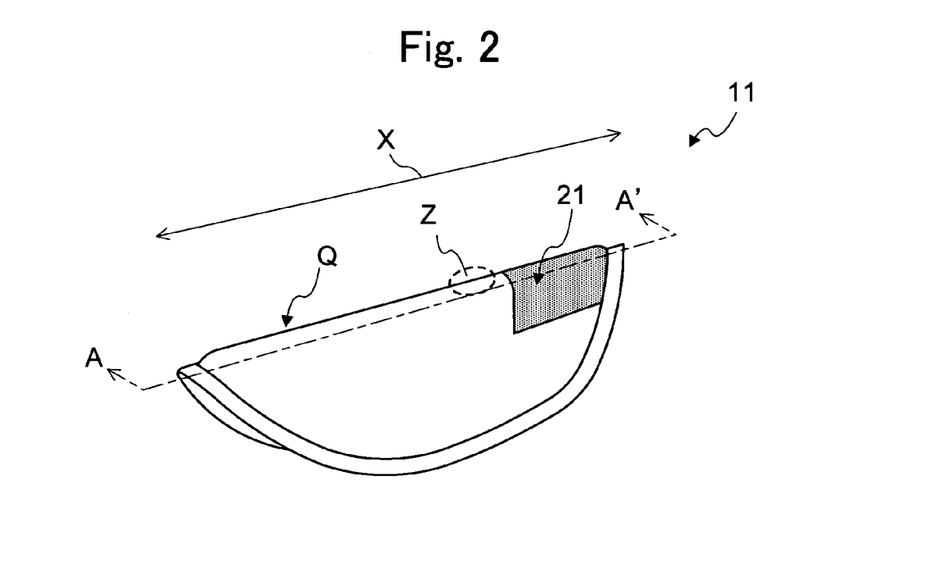
FIG. 2 is a perspective view of an interlabial pad 11, folded in two, relating to Embodiment 1.

FIG. 2 is a perspective view of an interlabial pad 11 relating to Embodiment 1, folded in two. The interlabial pad 11 of the present embodiment has a central axis Q extending along a longitudinal direction X. The pad 11 is folded in two, with the central axis Q as a folding line, and is worn with at least one portion held between labia minora of the labia, so that at least one portion close to the central axis Q touches a vestibule floor inside the labia. In addition, the pad 11 is provided with a rear portion low compression rigidity structure, by which the rear portion that is positioned to the rear of a wearer, and that touches the body of the wearer first when worn, has low compression rigidity in comparison to a front portion positioned to the front, so that the rear portion of the pad has a low compression rigidity portion 21.

Figure 3:
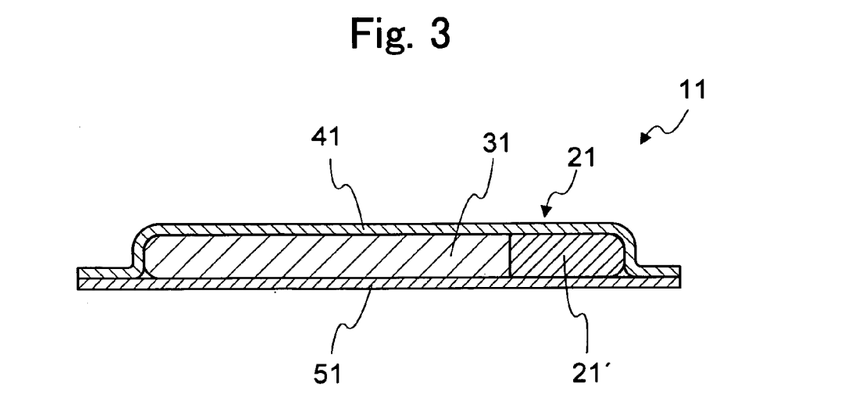
FIG. 3 is a cross-sectional view at A-A' in FIG. 2.

FIG. 3 is a cross-sectional view of FIG. 2 at A-A'. As shown in FIG. 3, the interlabial pad 11 of the present embodiment is provided with an absorbing body 31, a fluid permeable top sheet 41, and a back sheet 51, disposed on either side thereof. Furthermore, a portion 21' of the absorbing body 31 positioned to the rear of the wearer serves as the rear portion low compression rigidity structure, and forms rear portion low compression rigidity structure 21 that has low compression rigidity in comparison to the front portion positioned to the front.

The interlabial pad 11 may have a shape suitable for the labia, such as an elliptical shape, a gourd shape, a teardrop shape, or the like. Regarding the overall dimensions of the outer form of the interlabial pad 11, the width in the longitudinal direction X is preferably between 40 and 180 mm, and more preferably between 80 and 120 mm. Additionally, the width in a direction perpendicular to the central axis Q is preferably between 20 and 100 mm, and more preferably between 50 and 80 mm. Furthermore, the width in the direction perpendicular to the central axis Q is the dimension of the interlabial pad 11 in a flat state before being folded in two, and when the interlabial pad is worn in a folded state, the dimension in a vertical direction when worn is approximately ½ the size of the abovementioned width. Moreover, as described above, the interlabial pad 11 is of a type in which a flat pad is folded in two and held between the labia; however, other forms such as a rod shape or a cylinder shape are possible. In pads other than the type in which the flat pad is folded in two when worn, the width in the direction perpendicular to the central axis is approximately ½ the abovementioned width. In addition, the thickness of the pad (the thickness in a direction horizontal with the body when the pad is held between the labia) is preferably between 4 and 12 mm, and more preferably between 6 and 8 mm.

The average length of the pudendal cleft (from anterior labial commissure to the posterior labial commissure) is about 80 mm, the average length from the clitoris to the vaginal opening is about 40 mm, and the average length from the vaginal opening to the anus is about 45 mm (based on research by the inventors). In order to prevent leakage of menstrual blood, the front border of the interlabial pad preferably covers at least as far as the clitoris, and in order to prevent the pad dropping out due to movement of posterior muscles, the rear border preferably does not reach the anus. In order to fulfill these conditions, the overall dimensions of the outer form of the interlabial pad are preferably within the abovementioned ranges.

Low Compression Rigidity Portion

In the present invention, the low compression rigidity portion is a portion of the pad that has low compression rigidity, and denotes "a region that can indent first, in a direction away from the body". The low compression rigidity portion can be provided with various types of "rear portion low compression rigidity structure", in order that, as a result, the compression rigidity of the pad be low.

As shown in FIG. 2, in the present embodiment, the low compression rigidity portion is arranged more towards the rear than the vicinity of the vaginal opening contact area Z on the central axis. In this way, when the pad is worn, when the posterior labial commissure of the wearer comes in contact with the rear portion of the pad, the rear portion of the pad indents first. Accordingly, the pad does not deform irregularly when worn, and the central axis of the pad can be made to fit the vestibule floor.

The vaginal opening contact area Z is preferably arranged to be in an area extending from the middle of the central axis of the pad to 5 mm in front of the rear edge border of the pad. If it is more towards the front than the middle of the central axis, the front of the pad cannot cover the clitoris, or the rear portion of the pad ends up reaching as far as the anus. On the other hand, if arranged more to the rear than 5 mm in front of the rear edge border of the pad, menstrual blood discharged from the vaginal opening leaks from the rear portion of the pad. The low compression rigidity portion of the present invention is "a region that can indent first, in a direction away from the body", and since it is arranged between a point to the rear of the vicinity of the vaginal opening contact area Z and the rear edge in the present embodiment, at least one part thereof is arranged between a portion to the rear of the middle of the central axis of the pad and the rear edge of the pad.

The low compression rigidity portion is preferably arranged from a position between 5 and 40 mm from the rear edge border of the pad, along the central axis, in the direction of the rear border of the pad. More preferably, it is arranged to extend as far as the rear edge border. Additionally, the dimension of the "low compression rigidity portion which can indent first, in a direction away from the body" is preferably 4 mm or greater in directions towards the left and right side borders, straddling the central axis, and more preferably 7 mm or greater. It may be arranged to extend as far as the left and right borders of the pad. If smaller than 4 mm, since the depth from the posterior labial commissure to the body side of the vaginal opening is between about 4 and 8 mm (based on research by the inventors), if the central axis of the pad is made to fit the vaginal vestibule floor, the pad deforms irregularly.

Compression Rigidity Value of Low Compression Rigidity Portion

A "low compression rigidity portion that can indent first, in a direction away from the body" has low compression rigidity, compared to the front portion positioned towards the front. Here, using a measuring instrument manufactured by Kato Tech, Co., Ltd., (KES-5 Handy-Type Compression Tester), based on a measuring method by a KES system, the compression rigidity is expressed as a compression rigidity value measured under conditions of a load of 100 g/cm$^2$, a compression terminal area of 1 cm$^2$, a terminal speed of 0.1 cm/sec, and a gap of 20 mm. More specifically, under these conditions, as shown in FIG. 1, with the pad 1 fixed to a measuring table 101 using tape 102 so that a measuring height range from the central axis of the pad 1 is 20 mm, this is a force required to compress the central axis of the pad 1 by 3 mm in a vertical direction when worn.

The difference between the low compression rigidity portion 21 of the rear portion and the compression rigidity value of the front portion is preferably greater than or equal to 0.1 N/cm$^2$ and less than or equal to 0.9 N/cm$^2$. More preferably, it is greater than or equal to 0.15 N/cm$^2$ and less than or equal to 0.5 N/cm$^2$.

Rear Portion Low Compression Rigidity Structure

The "rear portion low compression rigidity structure" in Embodiment 1 will be explained. The "rear portion low compression rigidity structure" is a structure which leads to configure the compression rigidity value of the rear portion of the pad 11 to be lower than the compression rigidity value of the front portion. In Embodiment 1, as the "rear portion low compression rigidity structure", a slit is provided with the absorbent body 31.

Figure 4:
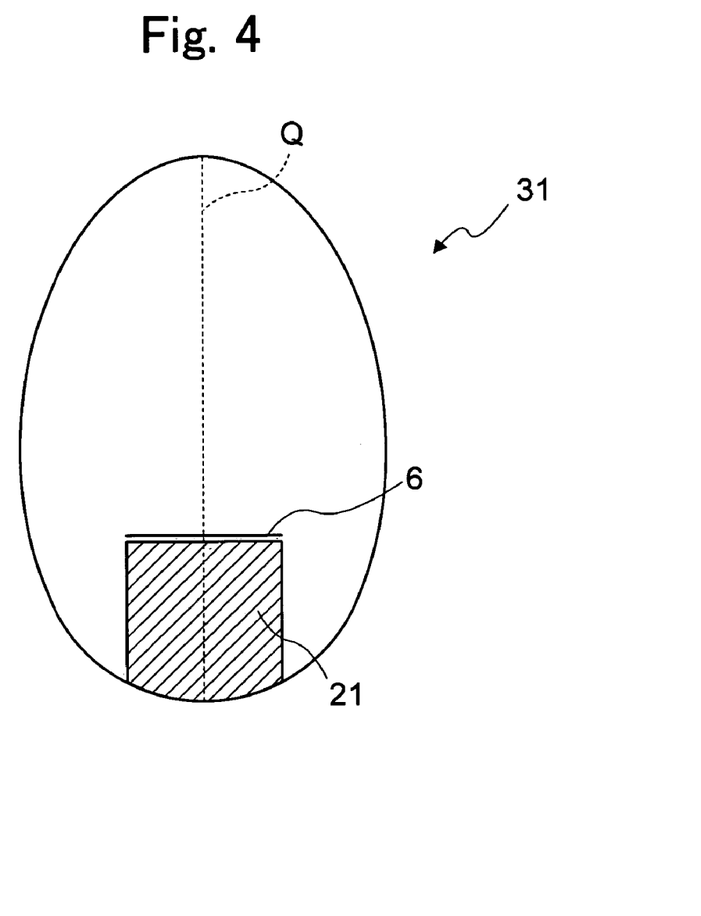
FIG. 4 is a plan view of an absorbent body 31 of the interlabial pad 11 relating to Embodiment 1.
Figure 5:
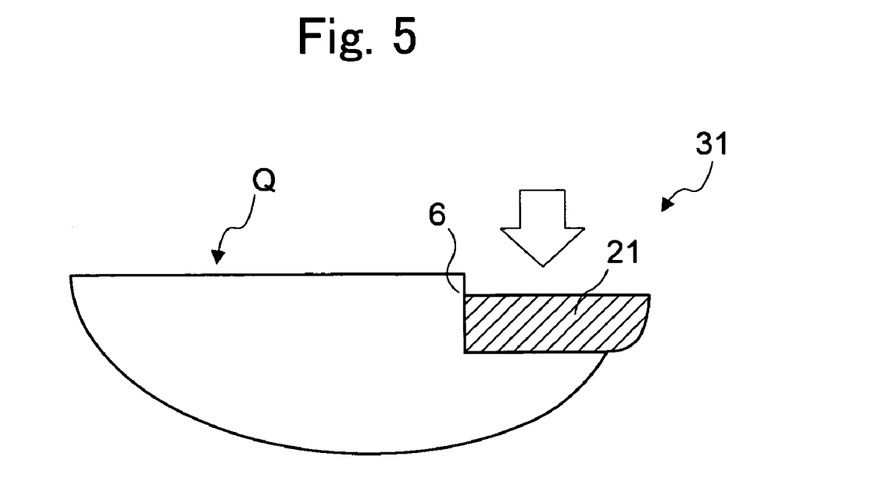
FIG. 5 is a view explaining behavior of a slit 6 of the interlabial pad 11 of Embodiment 1.
Figure 6:
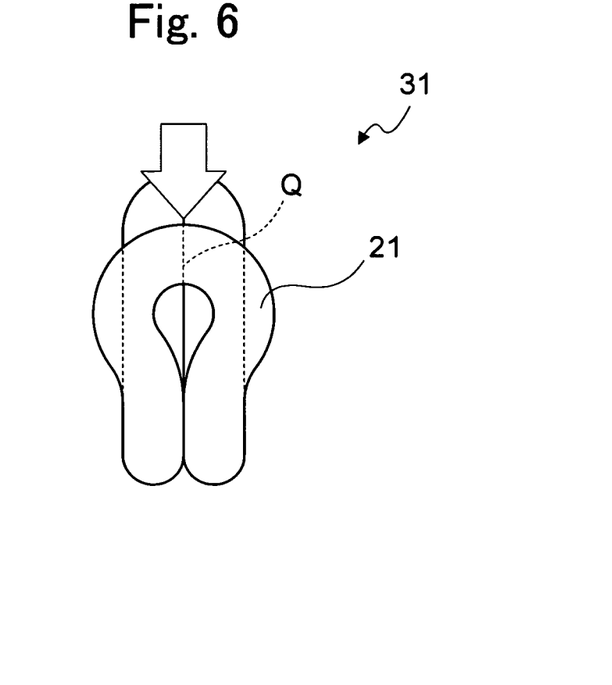
FIG. 6 is a view explaining the behavior of the slit 6 of the interlabial pad 11 of Embodiment 1.

FIG. 4 is a plan view of the absorbent body 31 of the interlabial pad 11 relating to Embodiment 1. In order to explain the action of the slit 6 in the interlabial pad 11 relating to Embodiment 1, FIG. 5 is a side view of a state when a compression force is applied in a vertical direction to the rear portion of the folded absorbent body 31. Additionally, FIG. 6 is a view of the state at this time, from a rear side. In Embodiment 1, by providing the slit 6, the shape is such that indentation is triggered in a direction away from the body.

The slit 6, as shown in FIG. 4, is arranged in a region straddling the central axis Q. In Embodiment 1, by arranging the slit 6 in a region straddling the central axis Q, the rigidity in the longitudinal direction of the pad 11 is divided by the slit 6. In this way, when the posterior labial commissure of the wearer comes in contact with a part of the central axis Q positioned at the rear of the pad 11 when it is folded in two, by the existence of the slit 6, only the part of the central axis Q positioned at the rear side of the pad 11 indents and receives a compressing action (see FIG. 5 and FIG. 6). At this time, since a part of the central axis Q positioned at the front side of the pad 11, and positioned more to the front than the slit 6, is separated from the part of the central axis Q positioned at the rear side, by the slit 6, it comes in contact with the posterior labial commissure area, and impacts received by the pad 11 are not transmitted. As a result, the front portion of the pad 11 when worn is not compressed in a vertical direction, and can be made to fit the vestibule floor.

The slit 6 used as the "rear portion low compression rigidity structure" in Embodiment 1, in cases in which it is arranged in one place only, is preferably arranged so that it is symmetrical to the central axis Q, in a direction approximately perpendicular to the central axis Q. Additionally, the slit 6 may be arranged in one place only; however, multiple slits may also be disposed, arranged discontinuously at intervals, in a region straddling the central axis Q, from the rear portion of the pad 11 to the rear edge border. By arranging multiple slits 6 discontinuously, at intervals, in cases in which contact occurs with the posterior labial commissure area of the wearer when the pad is worn, even with only a slight force, the rear portion of the pad 11 is easily compressed, and the pad 11 can be prevented from deforming irregularly.

In order to configure the "low compression rigidity portion 21 that can indent first, in a direction away from the body", the slit 6 dimension is preferably 4 mm or greater. Furthermore, the slit 6 may extend to the left and right borders of the absorbent body 31. In cases in which multiple slits 6 are arranged, the slits 6 are preferably at intervals of 1 mm or more, in the longitudinal direction. If they are arranged at intervals of less than 1 mm, it is difficult to maintain the pad 11 shape. Additionally, in cases in which multiple slits 6 are arranged, the arranged slits 6 need not be approximately parallel; a combination of a slit pattern in the longitudinal direction and a slit pattern in a direction perpendicular to the longitudinal direction, or crossover thereof, or in addition, mixed with patterns in an oblique direction, are also possible. Furthermore, the slit 6 is not limited to a linear pattern, nor are there particular limitations to a curved pattern, a wave pattern, or the like.

In Embodiment 1, if the slit 6 extends through the absorbent body 31, it is preferable that behavior as shown in FIG. 5 and FIG. 6 be easily induced; however, in order to have a form that triggers indenting in a direction away from the body, the slit need not necessarily extend through the absorbent body 31, and it is sufficient that half or more of the thickness of the absorbent body be cut by the slit 6.

Absorbent Body

Material for the absorbent body 31 provided in the interlabial pad 11 is preferably pulp, chemical pulp, rayon, acetate, natural cotton, a polymer absorbent body, a fibrous polymer absorbent body, synthetic fiber, foam, or the like, either separately or in a mixture, and is bulky, does not easily lose shape, and gives little chemical irritation. Furthermore, in order to have compression without giving a foreign-object sensation to the wearer, bulky material is preferable. For example, synthetic fibers or the like, can be mainly used, formed of compounds of physically embossed rayon or acetate, chemical pulp bridged by a cross-linking agent and crimped, or core-in-sheath type, off-center core-in-sheath type, side-by-side type compounds that use thermal shrinkage ratios of resins such as polyethylene (PE), polypropylene (PP), or polyethylene terephthalate (PET). In addition, these materials have improved molecular orientation by being stretched when spun, and mixtures of variant forms that are Y-shaped or C-shaped in cross-section are also possible. Furthermore, in order to improve smoothness between fibers, oil may be coated or included in the fiber.

In the absorbent body 31 these fibers can be opened and built up in layers. These fibers may be made in a single layer, or alternatively, in order to hold the menstrual blood, a multilayered type may be used, in which the lower layer side has more hydrophilic fiber than the upper layer. In addition, for example, the fiber may be formed as a sheet by an air laid method, a spunlace method, a paper making method, a melt blown method, or the like, and after that, the fiber may be woven by carrying out a needling process. Alternatively, the fiber that has been formed into a sheet may be passed between rolls with dot-pattern, grid-pattern, or wave-pattern, and be subjected to embossment processing.

Top Sheet

The top sheet 41 preferably is extendable in the longitudinal direction. In this way, when the rear portion of the pad 11 is compressed on making contact with the posterior labial commissure, a problem of the pad 11 deforming irregularly resulting from the top sheet 41 not being able to extend can be prevented. Furthermore, the portion that is made extensible may be the whole of the top sheet 41, or extensibility may be partly given, close to the "low compression rigidity portion that can indent first, in a direction away from the body".

As a method for providing extensibility in the longitudinal direction, for example, a broken line substantially parallel to the lateral may be arranged discontinuously on the top sheet 41, but there is a danger than the absorbent body 31 may drop out, or the inner wall of the labia may be harmed. Due to this, the top sheet 41 is preferably configured as below, providing extensibility in the longitudinal direction.

Examples of material of which the top sheet 41 is formed include: thermoplastic resin such as polyethylene, polypropylene, polyethylene terephthalate, or the like, each resin alone, or as a synthetic fiber of a core-in-sheath type, an off-center core-in-sheath type, or a side-by-side type compound, or cellulosic hydrophilic fibers such as pulp, chemical pulp, rayon, acetate, or natural cotton. These fibers can be made into non-woven fabric, alone or as compounds, by hydroentanglement, spunbond, point bond, through-air, or the like, to be used in the top sheet 41. As a specific example of the top sheet 41, a fiber mix with ratios of 50% to 95% rayon or acetate, and 5% to 50% polyethylene te-rephthalate, accommodated in a range of 20 to 60 g/m$^2$ in spunlace non-woven fabric, or extensible spunbond non-woven fabric may preferably be used.

Furthermore, in the top sheet 41, with a clamp interval of 100 mm, and low speed extension at a tension speed of 100 m/minute, when the extension rate in a longitudinal direction is 5%, stress is preferably between 0.01 and 0.5 N/25 mm. If the stress at an extension rate of 5% in the longitudinal direction is lower than 0.01 N/25 mm, it is difficult to maintain the shape as a sheet; on the other hand, if it is higher than 0.5 N/25 mm, the top sheet 41 becomes taut at the "low compression rigidity portion 21 that can indent first, in a direction away from the body", impeding the rear portion of the pad 11 from compressing.

When the top sheet 41 is formed by hydroentanglement, by carrying out entanglement of the fiber with flowing water at low water pressure, binding force between the fibers can be moderated. Specifically, the sheet is preferably made at a water pressure of 4.9 mN/cm$^2$ or less. In addition, in cases in which synthetic fiber is mixed in, in the drying process after the hydroentanglement, the drying temperature is preferably made lower than the softening point of the synthetic fiber.

At the stage of producing the top sheet 41, as above, the top sheet 41 may be formed to have extensibility; however, by applying processing to moderate the binding force between the fibers, extensibility may be given to a sheet with poor extensibility (a sheet with stress higher than 0.5 N/25 mm). If the binding force between the fibers is moderated, the freedom of each fiber is increased, so that in the "low compression rigidity portion 21 that can indent first, in a direction away from the body", when the rear portion of the pad 11 is compressed, the fiber forming the top sheet can move, and by the top sheet 41 becoming taut, it is possible to avoid inhibiting the compression.

As methods that can be cited for moderating the binding force between the fibers of the fiber assembly constituting the top sheet 41, after forming the top sheet 41, the sheet is given tendering treatment, or by carrying out wave pattern embossment processing on the sheet, the sheet generated is moderated. This processing may be carried out on the whole sheet, or may be done on parts, close to the "low compression rigidity portion 21 that can indent first, in a direction away from the body"; however, in order to maintain the form of the sheet and support attachment of the top sheet 41 to the inner wall of the labia, since flatness characteristics of the top sheet 41 must be retained, processing in parts is preferable.

Furthermore, even if the fibers of the top sheet 41 are not moderated, by folding the top sheet 41 so that creases can be formed in a direction perpendicular to the central axis, or by making corrugations to form grooves extending in a direction perpendicular to the central axis, a configuration may be made in which extension in the longitudinal direction is possible. In such cases, the creases should preferably be 1 mm or greater; if narrower than 1 mm, when the pad 11 bends in the longitudinal axis direction, it cannot extend sufficiently. Furthermore, as an example of corrugation processing, it is preferable that the interval between grooves be between 0.5 and 3 mm, and that the depth of the grooves be between 0.1 and 3 mm. Moreover, as another example, for a sheet that is poor in extensibility (having a stress of 0.5 N/25 mm or greater), a material that can extend in the longitudinal direction may be joined to a portion located at the "low compression rigidity portion 21 that can indent first, in a direction away from the body". The extensible material may be selected from among the materials described above.

Back Sheet

In the present invention, in the "low compression rigidity portion 21 that can indent first, in a direction away from the body", in order not to block the rear portion of the pad 11 from being compressed, the back sheet 51 is preferably extensible in the longitudinal direction, at least in the vicinity of the "low compression rigidity portion 21 that can indent first, in a direction away from the body".

In addition, the back sheet 51 is preferably impermeable, through which body fluids do not pass. For the back sheet 51, for example, 15 to 60 micrometer thick polyethylene, polypropylene, polyethylene terephthalate, polyvinyl alcohol, polylactic acid, polybutyl succinate, or non-woven fabric, paper, or a laminated material thereof may be cited. In addition, the back sheet may be an air permeable film obtained by loading resin with inorganic filler and extending. Specifically, film made mainly of low density polyethylene resin, prepared with a basis weight per unit area in a range of 15 to 30 g/m$^2$, and additionally, air permeable film with an open pore area ratio of 10% to 30%, and pore diameter in a range of 0.1 to 0.6 mm, may be cited. Furthermore, non-woven fabric can be used, and spunbond non-woven fabric, point bond non-woven fabric, through-air non-woven fabric, and the like, may be cited, and these may be given a water repellent finish.

As a method of providing extensibility, for example, for these materials, corrugated processing may be carried out, with grooves formed in a direction perpendicular to the central axis, at least in the "low compression rigidity portion 21 that can indent first, in a direction away from the body". Other methods of providing extensibility that may be used include insertion of line cuts, cutting out a circular shape, opening of pores, or the like; however, from the viewpoint of fluid impermeability, corrugation processing is preferable.

Method of Manufacturing of Interlabial Pad 11

The interlabial pad 11 of the present invention is obtained by joining the absorbent body 31, the top sheet 41, and the back sheet 51. As a joining method, for example, a method in which heat is added when embossment is being performed, and heat sealing of the absorbent body 31, the top sheet 41, and the back sheet 51 carried out, or a method of joining by an adhesive, may be cited, and these methods may be used alone or in combination.

In cases in which joining is performed by embossment processing, the embossment pattern is not particularly limited, and a dot pattern, a grid pattern, a wave pattern, or the like, may be suitably selected. Among these, since a foreign-object sensation is not excessively given to the inner walls of the labia, joining with the dot embossment pattern at an area ratio of 10% is preferable.

In cases of joining by heat sealing, heat may be added at a temperature at or above the softening point of the component material, and heat embossment processing, ultra sound wave processing, or the like, may be cited.

In cases of joining using an adhesive, examples that may be cited include: a rubber-based adhesive such as SEBS, SBS, or SIS, a heat sensitive adhesive or a pressure-sensitive adhesive composed mainly of olefin series material such as linear low-density polyethylene, or a water sensitive adhesive that is a water-soluble polymer such as polyvinyl alcohol, carboxymethyl cellulose, or gelatine, or that is a water swelling polymer such as polyvinyl acetate, or sodium polyacrylate. Among these, when body pressure acts on the interlabial pad 11, even in a case where the adhesive seeps out to the outer face of the interlabial pad 11, since at that point in time the pad is not tuckable, the heat sensitive adhesive is preferable. As a specific example of the adhesive, a melt mixture may be cited having 5% to 25% SEBS, 40% to 60% alicyclic saturated hydrocarbon, 1% to 10% aromatic modified terpene, and 15% to 35% admixture.

For the coating pattern of the adhesive, spiral coating, controlled seam coating, coater coating, curtain coater coating, and Summit gun coating may be cited. The adhesive coating quantity is preferably in the range 1 to 30 g/m$^2$, and more preferably in the range 3 to 10 g/m$^2$. For a pattern in which the adhesive is coated linearly, the line width is preferably in a range of 30 to 300 micrometers. In cases in which the adhesive coating quantity is less than 1 g/m$^2$, or the line width is less than 30 micrometers, if the top sheet 41 is formed of a fiber aggregate, since the adhesive will be buried between the fibers, sufficient joining strength is not obtained. On the other hand, in cases in which the adhesive coating quantity is greater than 30 g/m$^2$, or the line width is larger than 300 micrometers, the periphery of the portion on which the adhesive is applied becomes stiff. If the coating of the adhesive is performed on at least one portion or at all portions on the periphery of the pad 11, there is no particular limitation; however, in consideration of the absorption of fluid, it is preferable to apply the coating on at least one portion or on all portions of the periphery, on the back face of the absorbent body 31.

Function and Effects

In the present embodiment, by arranging the portion that can easily indent in a direction away from the body, more to the rear than, at least, an area that touches the vaginal opening, on the central axis of the pad 11, when the pad 11 is worn interlabially, even if the rear portion of the pad 11 touches the posterior labial commissure, the region that is in contact with the posterior labial commissure, indents first, and the central axis of the pad 11 can be made to fit the vaginal opening and the vestibule floor.

EMBODIMENT 2

Embossment

An interlabial pad relating to Embodiment 2 will now be explained. In Embodiment 2, as the "rear portion low compression rigidity structure", an embossment 7 is provided with the absorbent body 32. In Embodiment 2, by providing an embossment 7, with the embossment area given high rigidity, as a trigger for the embossment area to bend, it is possible to arrange that the rear portion of the pad only compresses first.

Rear Portion Low Compression Rigidity Structure

Figure 7:
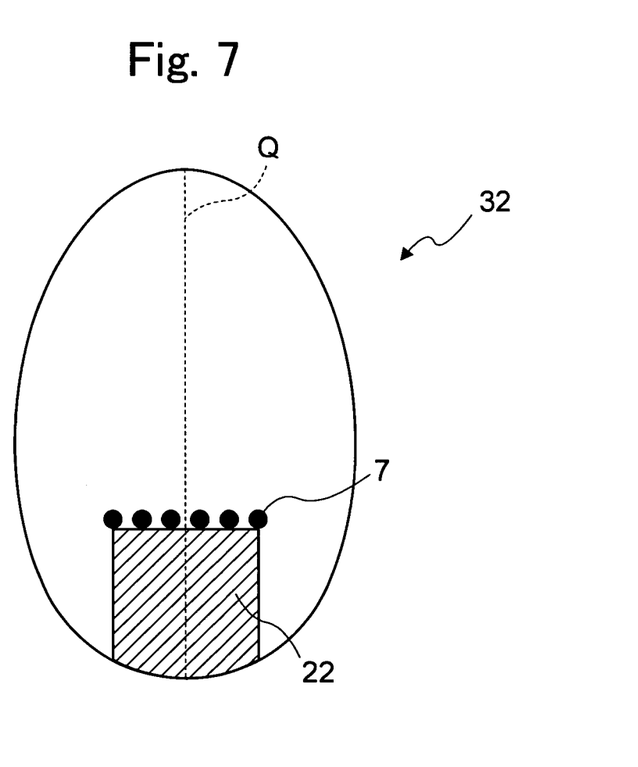
FIG. 7 is a plan view of an absorbent body 32 of an interlabial pad relating to Embodiment 2.
Figure 8:
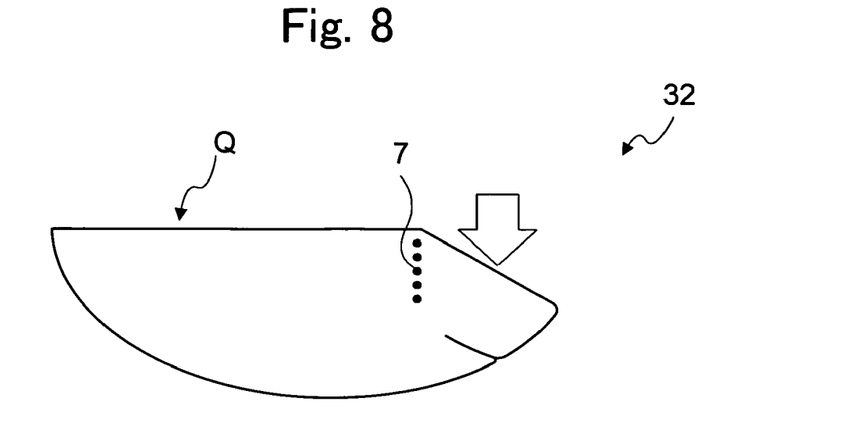
FIG. 8 is a view explaining behavior of an embossment 7 of the interlabial pad relating to Embodiment 2.

FIG. 7 is a plan view of an absorbent body 32 of an interlabial pad related to Embodiment 2. In Embodiment 2, the embossment 7 is arranged in a discontinuous row in a direction perpendicular to the direction of the central axis Q. Furthermore, to explain the behavior of the embossment 7 in Embodiment 2, FIG. 8 is a side view with compression force applied in a vertical direction to the absorbent body 32 that is folded in two.

As shown in FIG. 7, the embossment 7 is implemented discontinuously in an area straddling the central axis Q. By providing the embossment 7, the area given the embossment 7 has high density in parts, so that a difference in rigidity is arranged in the longitudinal direction of the pad. In this way, the area given the embossment 7 exists as a border between the front portion and the rear portion of the pad, and the rigidity of the area between the front portion and the rear portion of the pad is high, therefore even in cases in which the rear portion of the pad when worn is in contact with the posterior labial commissure of the wearer and is compressed in a vertical direction, by the existence of the embossment 7 that has high rigidity, impacts that the pad receives due to being in contact with the posterior labial commissure are not easily transmitted to the front portion of the pad. As a result, low compression rigidity portion 22 is provided at the rear portion of the pad, and the front portion of the pad is not compressed, and can be made to fit the vestibule floor.

Moreover, the embossment 7 may be arranged as a discontinuous row in the direction perpendicular to the central axis Q (see FIG. 7); however, in the present invention, this does not imply a limitation, and multiple rows may be provided, or a continuous pattern may be arranged approximately perpendicular to the central axis Q.

The embossment pattern arranged on the pad related to Embodiment 2 is not limited to a dot pattern, a grid pattern, a wave pattern, or the like, and for example, it may be obtained by passing paper between an embossment roll with convex shapes, and a flat roll. A specific example of a convex shape is a form with a height in a range of 0.1 to 2 mm, an area in a range of 0.2 to 20 mm$^2$, and at a spacing in a range of 0.2 to 20 mm. More specifically, an embossment pattern may be cited having neighboring embossment dot patterns with an area of 2 mm$^2$, the neighboring embossment portions being at a spacing of 7 mm, and the embossment portions being arranged at an angle of 45 degrees.

The area in which the embossment 7 is provided in Embodiment 2 will now be explained. The area in which the embossment 7 is arranged is preferably an area extending from a position between 5 and 40 mm from the rear of the pad, towards the front edge of the pad. In addition, the area of the embossment 7 in the longitudinal direction is preferably greater than or equal to 0.5 mm and less than or equal to 175 mm, and more preferably an area greater than or equal to 5 mm and less than or equal to 40 mm. By arranging the embossment 7 area in the longitudinal direction at 0.5 mm or greater, it is possible to make a trigger so that it indents first. Moreover, at most, the embossment 7 may be arranged up to the front edge of the pad; however, so as not to give a foreign-object sensation to the wearer, it should preferably be arranged at 40 mm or less. In addition, the embossment 7 area in the direction perpendicular to the central axis Q is preferably an area greater than or equal to 2 mm and less than or equal to 50 mm, approximately equal on the left and the right of the central axis Q. More preferably, it is greater than or equal to 3 mm and less than or equal to 10 mm. If the length is less than 2 mm from the central axis Q, an action in which indenting first is triggered, is not possible. Moreover, at most, the embossment 7 may be arranged up to the left and right edges of the pad; however, so as not to give a foreign-object sensation to the wearer, it should preferably be arranged at 10 mm or less. In addition, the embossment 7 need not be given to the absorbent body only, and embossment processing may be implemented on the top sheet or the back sheet or both sheets.

Modified Example of Embodiment 2

Figure 9:
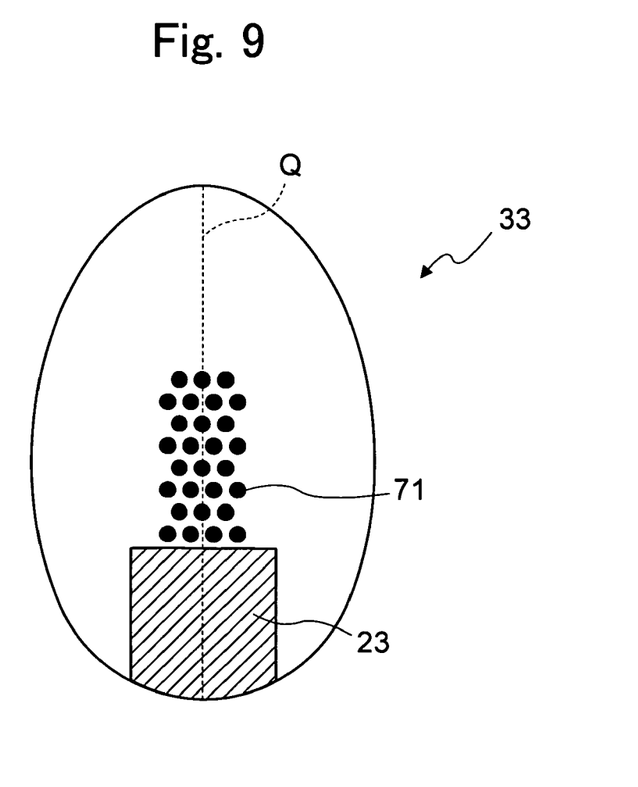
FIG. 9 is a plan view of a modified example of an absorbent body 33 in Embodiment 2.

FIG. 9 is a plan view of an absorbent body 33 of an interlabial pad related to a modified example of Embodiment 2. In the absorbent body 33 shown in FIG. 9, embossments 71 are disposed adjacently and discontinuously, at intervals, in an area extending more towards the front than the center point of the central axis Q. In the pad using this type of absorbent body 33, the rigidity of the low compression rigidity portion 23, the portion that makes contact more to the rear than the posterior labial commissure when worn, is lower than the rigidity of the portion that fits the vestibule floor so that the rear portion of the pad is compressed easily, and can bend easily in a direction away from the body, first.

EMBODIMENT 3

Area with Low Basis Weight Per Unit Area

An interlabial pad related to Embodiment 3 will now be explained. In Embodiment 3, an absorbent body with varied basis weight per unit area for the front portion and the rear portion is used for the "rear portion low compression rigidity structure". In Embodiment 3, by varying the basis weight per unit area between the front portion and the rear portion of the absorbing body of the pad, a shape that triggers bending is formed, and the arrangement is such that the rear portion of the pad only can compress first.

Rear Portion Low Compression Rigidity Structure

Figure 10:
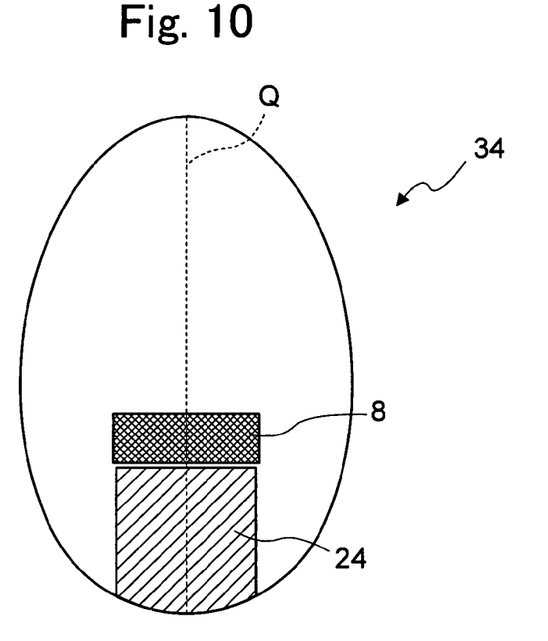
FIG. 10 is a plan view of an absorbent body 34 of an interlabial pad relating to Embodiment 3.

FIG. 10 shows the absorbent body 34 of the interlabial pad related to Embodiment 3. In Embodiment 3, an area 8 with a basis weight per unit area lower than in surrounding areas is arranged straddling the central axis Q in the rear portion. In the area 8, since the density is not made higher than neighboring areas, compression rigidity in a vertical direction of the wearer is lower than surrounding areas. In this way, when the interlabial pad is worn, if a part of the central axis positioned in the rear portion of the pad that is folded in two touches the posterior labial commissure of the wearer and a force acts in the vertical direction, with the area 8 in which the basis weight per unit area is lower than in surrounding areas as a trigger, the rear part of the pad rather than the area 8 is compressed in the vertical direction. Since impacts received by the pad on touching the posterior labial commissure are not easily transmitted to the pad positioned to the front of the area 8, low compression rigidity portion 24 is provided at the rear portion of the pad, and the front portion of the pad is not compressed in the vertical direction and can be made to fit the vagina vestibule floor.

For the area 8 of the absorbent body, having the low basis weight per unit area, the difference in the basis weight per unit area of the area 8 and that of the surrounding area is preferably greater than or equal to 20 g/m$^2$ and less than or equal to 1000 g/m$^2$. More preferably, it is greater than or equal to 100 g/m$^2$ and less than or equal to 500 g/m$^2$. In cases in which the basis weight per unit area difference is less than 20 g/m$^2$, an arrangement forming a trigger for indenting in a direction away from the body is not attained, and on the other hand, for an arrangement with a basis weight per unit area difference of greater than 1000 g/m$^2$, when worn interlabially, the whole pad gives a very unpleasant foreign-object sensation and is not preferable.

The absorbent body 34 in Embodiment 3 may be formed, for example, using a material mixture of 85% 3.3 dtex rayon and 15% cotton, with the light coating area 8 having a basis weight per unit area of 100 g/m² and the surrounding area having a basis weight per unit area of 300 g/m². Furthermore, as an example of the manufacture of the absorbent body 34, a material mixture of 85% 3.3 dtex rayon and 15% cotton is laminated to give a basis weight per unit area of 200 g/m², and after that, a part to be the low basis weight per unit area 8 is cut out, and the same material is laminated to give a basis weight per unit area of 100 g/m², before fixing with dot embossment or the like. Moreover, the manufacturing method is not limited to the above, and the absorbent body may be composed of multiple layers, with varied densities, materials, manufacturing methods, and the like, for each layer. As an example of a method that may be cited, spunlace non-woven fabric formed of a material mixture of 85% 3.3 dtex rayon and 15% cotton laminated to give a basis weight per unit area of 200 g/m², and a material mixture of 70% rayon and 30% polyethylene terephthalate giving a basis weight per unit are of 45 g/m², is folded in two, a part corresponding to the low basis weight per unit area 8 cut out is added, and then fixing with dot embossment or the like is carried out.

EMBODIMENT 4

Material with High Compression Rigidity

Rear Portion Low Compression Rigidity Structure

Figure 11:
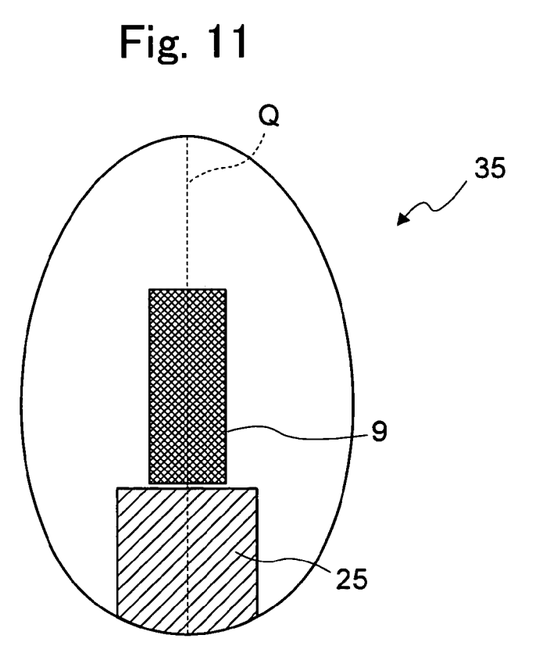
FIG. 11 is a plan view of an absorbent body 35 of an interlabial pad relating to Embodiment 4.

FIG. 11 shows an absorbent body 35 for an interlabial pad related to Embodiment 4. In Embodiment 4, material 9 with high compression rigidity is disposed in an area straddling a central axis Q. By disposing the material 9 with high compression rigidity on a part of the absorbent body 35, the low compression rigidity portion 25 is provided at the rear portion of the pad, and the rigidity of the portion that makes contact with the body when worn, more to the rear of the posterior labial commissure, is lower than the rigidity of the portion that fits the vestibule floor, so that the rear portion of the pad compresses easily, and the rear portion of the pad indents first, in a direction away from the body.

In an interlabial pad related to a modified example of Embodiment 4, the material 9 with the high compression rigidity is preferably disposed at a position at the approximate center of the central axis Q, more to the front than the low compression rigidity portion 25 that indents first, in a direction away from the body. This is the same area as the area in which the embossments 71 are provided with the absorbent body 33 of the interlabial pad related to the modified example of Embodiment 2 as shown in FIG. 9.

Besides the abovementioned materials for the absorbent body with low basis weight per unit area, the material 9 with high compression rigidity, for example, may be formed by layered pulp pressed to form embossment or the like, and after forming fiber of thermoplastic resin such as foamed polyurethane, polyethylene, polypropylene, or polyethylene terephthalate, either alone, or in a core-in-sheath type, an off-center core-in-sheath type, or a side-by-side type arrangement, a non-woven fabric made alone or in a composite, by hydroentanglement, spunbond, or the like, is formed either independently or laminated. Specifically, using non-woven fabric formed of polyethylene or polypropylene core-in-sheath 4.4 dtex fiber with fiber length of 51 mm, by a through-air method to give 20 g/m², this is laminated with pulp to give 200 g/m² that is then wrapped, and fixed by heat embossment to form an embossment pattern, with dot patterns having an area of 1 mm² and an interval of 3 mm between neighboring embossed portions, arrayed at an angle of 30 degrees.

EMBODIMENT 5

Joining

An interlabial pad related to Embodiment 5 will now be explained. In Embodiment 5, as a "rear portion low compression rigidity structure", a structure is used to join, among the sections that are folded in two and facing each other, the parts in the front portion. In Embodiment 5, by regulating the freedom of the pad between the front portion and the rear portion, a trigger for bending is formed, so that the rear portion of the pad only can be compressed, first.

Rear Portion Low Compression Rigidity Structure

Figure 12:
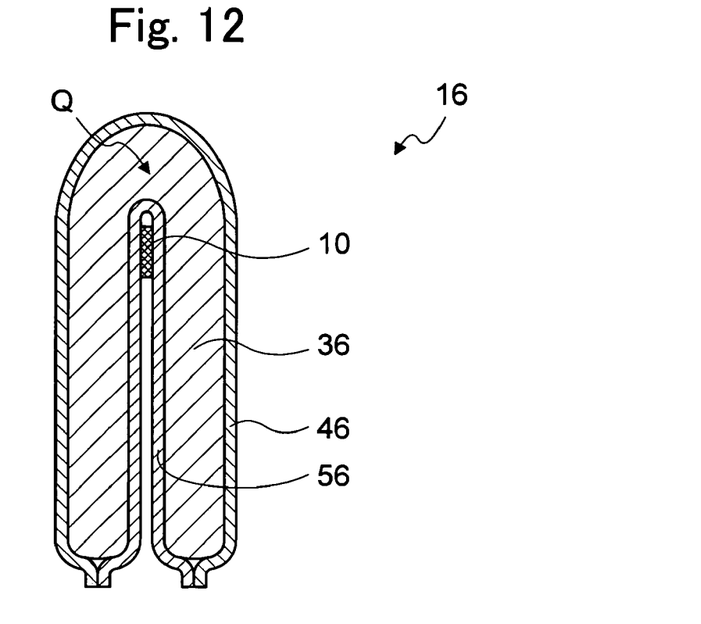
FIG. 12 is an explanatory view of a joining structure in a folded interlabial pad 16 relating to Embodiment 5.
Figure 13:
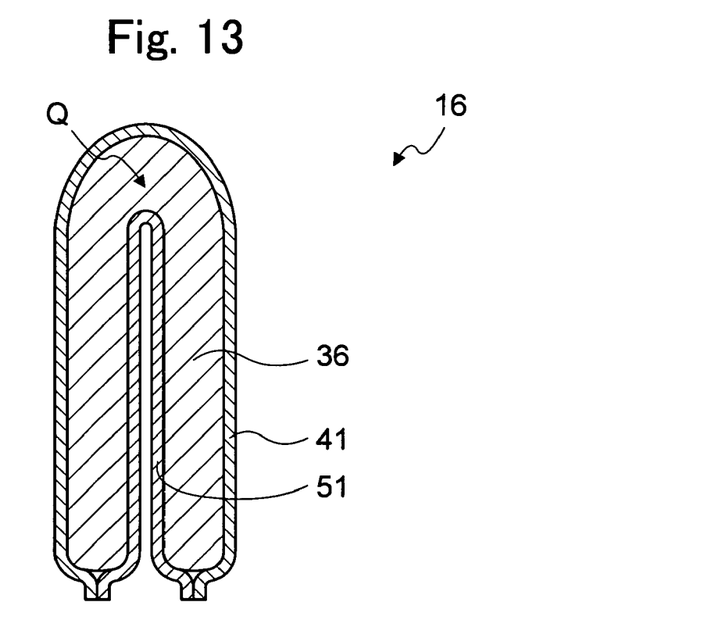
FIG. 13 is an explanatory view of the joining structure in the folded interlabial pad 16 relating to Embodiment 5.

FIG. 12 is a cross-sectional view of the front portion of the interlabial pad 16 related to Embodiment 5, folded in two, and cut in a direction perpendicular to the central axis Q. Similarly, FIG. 13 is a cross-sectional view of the rear portion of the interlabial pad 16 related to Embodiment 5, folded in two, and cut in a direction perpendicular to the central axis Q. In Embodiment 5, in the "rear portion low compression rigidity structure that can indent first, in a direction away from the body" the back face sections of the folded pad 16 are not joined, but in the portion to the front of the "rear portion low compression rigidity structure that can indent first, in a direction away from the body" the back face sections of the folded pad 16 are joined. In this way, when the pad 16 is worn, when force acts from the central axis Q in a vertical direction, since the "rear portion low compression rigidity structure that can indent first, in a direction away from the body" is not controlled, the pad can open from a folded state. On the other hand, since the front portion of the pad 16, at which the back face sections are joined, cannot open from a folded state, the compression rigidity in the vertical direction is high. As a result, when the rear portion of the pad 16 touches the posterior labial commissure, the rear portion of the pad 16 compresses easily, and it is possible to prevent the pad 16 from deforming irregularly.

As a method of joining the back face sections of the pad 16, for example, joining can be done using an adhesive, and heat sealing of the material parts can be done by adding heat when performing embossment, these processes being carried out in combination or alone. In cases in which the adhesive is used, the back face material sections can be directly joined. Examples of the adhesive that may be used include: a rubber-based adhesive such as SEBS, SBS, or SIS, a heat sensitive adhesive or a pressure sensitive adhesive composed mainly of olefin series material such as linear low-density polyethylene, or a water sensitive adhesive that is a water-soluble polymer such as polyvinyl alcohol, carboxymethyl cellulose, or gelatine, or that is a water swelling polymer such as polyvinyl acetate, or sodium polyacrylate.

As a specific example of the adhesive used for joining in Embodiment 5, a melt mixture may be cited, of 5% to 25% SEBS, 40% to 60% alicyclic saturated hydrocarbon, 1% to 10% aromatic modified terpene, and 15% to 35% admixture. In addition, well known methods may be used for the coating pattern of the adhesive, such as spiral coating, controlled seam coating, coater coating, curtain coater coating, or summit gun coating.

The adhesive coating quantity is preferably in the range 1 to 30 g/m², and more preferably in the range 3 to 10 g/m². For a pattern in which the adhesive is coated in a linear form, the line width is preferably in a range of 30 to 300 micrometers. In cases in which the adhesive coating quantity is less than 1 g/m², or the line width of the adhesive is less than 30 micrometers, sufficient joining strength cannot be obtained.

On the other hand, in cases in which the adhesive coating quantity is greater than 30 g/m², or the line width of the adhesive is larger than 300 micrometers, the manufactured pad becomes stiff, and a foreign-object sensation is given to the wearer.

In cases in which joining by embossment processing is done, the embossment pattern is not particularly limited to a dot pattern, a grid pattern, or a wave pattern; and with a dot embossment pattern, the top face material is joined in a state in which it is folded in two. In cases of joining by heat sealing, heat may be added at a temperature at or above the softening point of component materials, and heat embossment processing, ultrasonic processing, or the like, may be cited.

In the present invention, since if the top face material, the absorbent body, and the back face material were fixed, a foreign-object sensation would be easily given to the wearer, the adhesive is preferable as the joining method.

EMBODIMENT 6

Cutting

Figure 14:
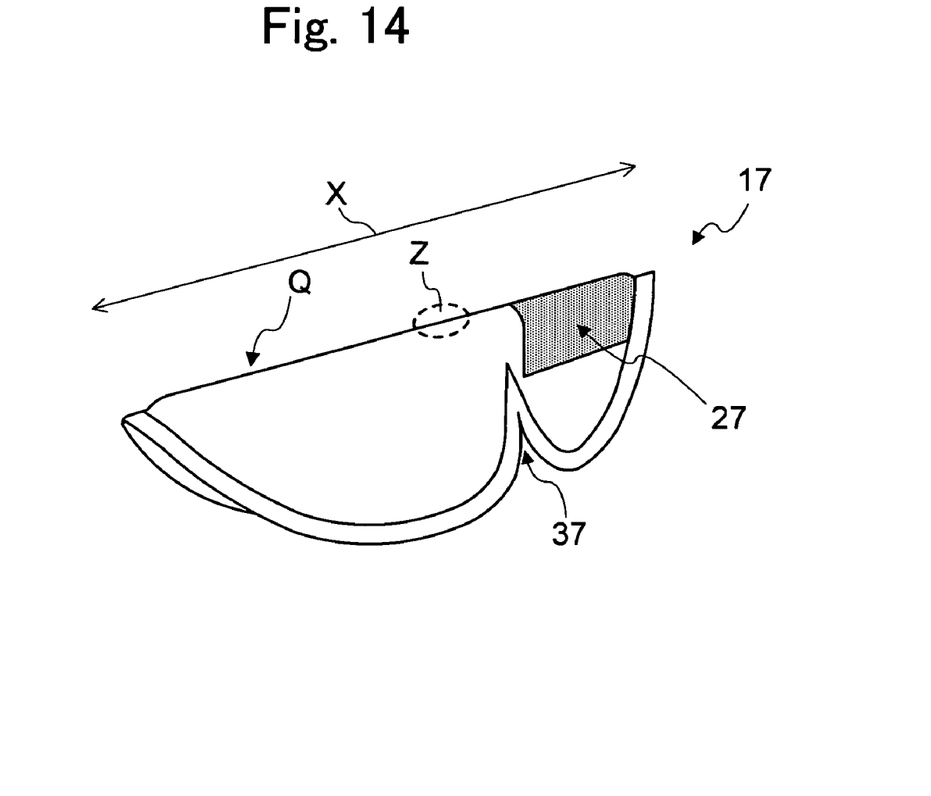
FIG. 14 is a perspective view of a folded interlabial pad 17 relating to Embodiment 6.

An interlabial pad 17 relating to Embodiment 6 will now be explained. In Embodiment 6, as a "rear portion low compression rigidity structure" a cutting 37 is used, extending from the border of the rear portion towards the central axis Q. The cutting 37 extends from the border towards In Embodiment 6, by the existence of the cutting, outside of the vicinity of the central axis Q, the front portion and the rear portion of the pad 17 are separated. As a result, when the interlabial pad 17 is worn, in cases in which the rear portion of the pad is in contact with the posterior labial commissure, the rear portion of the pad 17 in which the cutting is provided opens from a folded state, indents first, and is compressed.

Rear Portion Low Compression Rigidity Structure

FIG. 14 is a perspective view of the interlabial pad 17 folded in two, related to Embodiment 6. Since the rear portion of the pad 17 is smaller than the front portion, when the pad 17 is worn, in cases in which there is contact with the posterior labial commissure, the rear portion of the pad 17 opens easily, first, from a folded state.

In the present invention, the structure described above may be used alone as the "rear portion low compression rigidity structure"; however, use of a combination of multiple structures is also possible.

EMBODIMENT 7

Front Portion Low Compression Rigidity Structure

Figure 15:
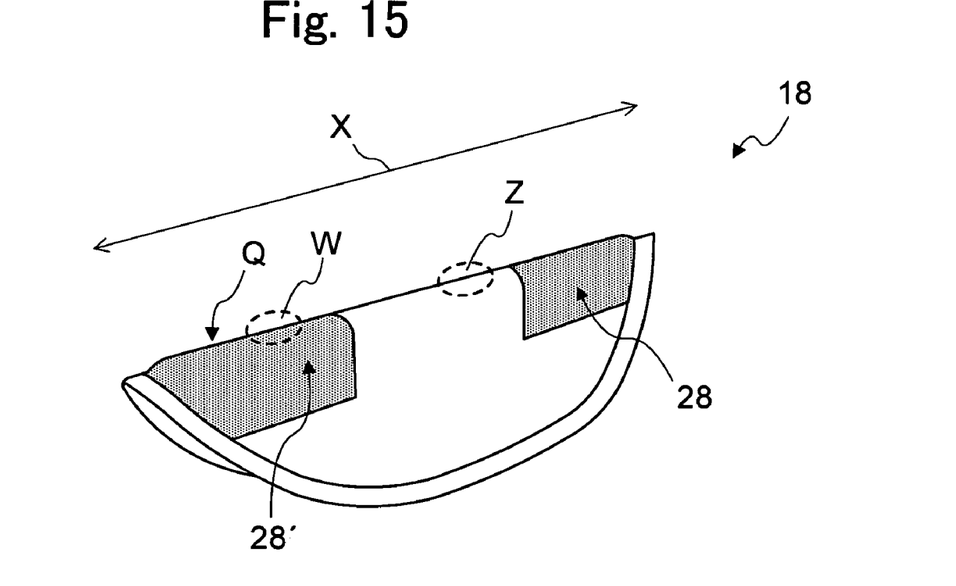
FIG. 15 is a perspective view of a folded interlabial pad 18 relating to Embodiment 7.

An interlabial pad 18 related to Embodiment 7 will now be explained. In Embodiment 7, besides the "rear portion low compression rigidity structure" a front portion low compression rigidity structure is provided at the same time. In this way, when the pad 18 is worn, not only in cases in which the rear portion of the pad 18 is in contact with the posterior labial commissure, but also in cases in which a clitoris contact area w positioned in the front portion of the pad 18 is simultaneously in contact with the clitoris, both the front portion and the rear portion can indent.

FIG. 15 shows the interlabial pad 18 related to Embodiment 7. According to FIG. 15, the front portion low compression rigidity structure is provided at the same time as the rear portion low compression rigidity structure, and the low compression rigidity portion 28 is arranged in the rear portion of the pad 18. Furthermore, another portion 28' with low compression rigidity is arranged in the front portion of the pad 18. The portion 28' with low compression rigidity in the front portion is preferably arranged in an area extending to the front edge, from a point greater than or equal to 20 mm and less than or equal to 50 mm, from the front of a border between the low compression rigidity portion 28 at the rear and other areas.

While preferred embodiments of the present invention have been described and illustrated above, it is to be understood that they are exemplary of the invention and are not to be considered to be limiting. Additions, omissions, substitutions, and other modifications can be made thereto without departing from the spirit or scope of the present invention. Accordingly, the invention is not to be considered to be limited by the foregoing description and is only limited by the scope of the appended claims.

What is claimed is:

1. An interlabial pad comprising:
   a top sheet and a back sheet, the interlabial pad being folded in two along a central axis extending along a longitudinal direction of the interlabial pad so that each of two folded parts of the back sheet faces the other of the two folded parts over an entire surface of the folded part;
   an absorbent body extending between the top sheet and the back sheet, the absorbent body including a front portion and a rear portion having a rear portion low compression rigidity structure; wherein
   a first material forming the front portion of the absorbent body has a higher compression rigidity relative to a second material forming the rear portion,
   the rear portion having the rear portion low compression rigidity structure and the front portion each have an upper surface located in a common plane when the interlabial pad is unfolded in non-wearing condition, and
   the rear portion low compression rigidity structure providing a low compression rigidity at the rear portion of the interlabial pad so that when the rear portion of the interlabial pad is positioned to the rear of a wearer and touches the body of the wearer first when worn, the rear portion is pushed by the body and indents before the front portion positioned to the front of the wearer.

2. The interlabial pad according to claim 1, wherein the rear portion has a compression stiffness value less than a compression stiffness value of the front portion, the difference therebetween being greater than or equal to 0.1 N/cm² and less than or equal to 0.9 N/cm².

3. The interlabial pad according to claim 1, wherein the rear portion low compression rigidity structure further comprises a slit arranged in a region straddling the central axis between the front portion and the rear portion.

4. The interlabial pad according to claim 1, wherein the rear portion low compression rigidity structure further comprises an embossment arranged in a region straddling the central axis between the front portion and the rear portion.

5. The interlabial pad according to claim 4, wherein the embossment extends discontinuously in a direction perpendicular to the central axis.

6. The interlabial pad according to claim 1, wherein
   the rear portion low compression rigidity structure is a part of the absorbent body which has a lower basis weight per unit area in a rear portion relative to that of a front portion.

7. The interlabial pad according to claim 1, wherein
   the rear portion low compression rigidity structure further comprises:
   a cut extending from a border of the rear portion, towards a center portion of the interlabial pad along the central axis, and wherein the cut has a prescribed width and does not reach the center portion.

8. The interlabial pad according to claim 1, further comprising a joining structure for joining parts of the two folded parts in the front portion.

* * * * *